United States Patent [19]

Koo

[11] 3,998,236
[45] Dec. 21, 1976

[54] DENTAL FLOSS MANIPULATOR

[76] Inventor: Bonny B. Koo, 1016 Austin Ave., Pacific Grove, Calif. 93950

[22] Filed: Aug. 15, 1975

[21] Appl. No.: 605,028

[52] U.S. Cl. .............................................. 132/92 R
[51] Int. Cl.² ........................................... A61C 15/00
[58] Field of Search .................. 132/92 R, 91, 40 R

[56] References Cited
UNITED STATES PATENTS

| | | | |
|---|---|---|---|
| 2,061,877 | 11/1936 | Naundorf | 132/92 R |
| 3,759,274 | 9/1973 | Warner | 132/92 R |

*Primary Examiner*—Robert Peshock
*Attorney, Agent, or Firm*—George B. White

[57] ABSTRACT

A dental floss manipulator which has a handle adapted to store a spool of dental floss and a fork on the free end of the handle adapted to hold the unwound dental floss under tension between the spaced fingers for insertion between the teeth; a resiliently yieldably held anchor in the handle holds the unwound dental floss under tension, and a trigger lever pivoted on the handle to which the free end of the unwound dental floss is fastened, is manipulatable against the action of the resiliently yieldable anchor to pull the dental floss between the fork fingers in opposite directions between the teeth without reciprocating the handle itself.

7 Claims, 3 Drawing Figures

U.S. Patent
Dec. 21, 1976
3,998,236
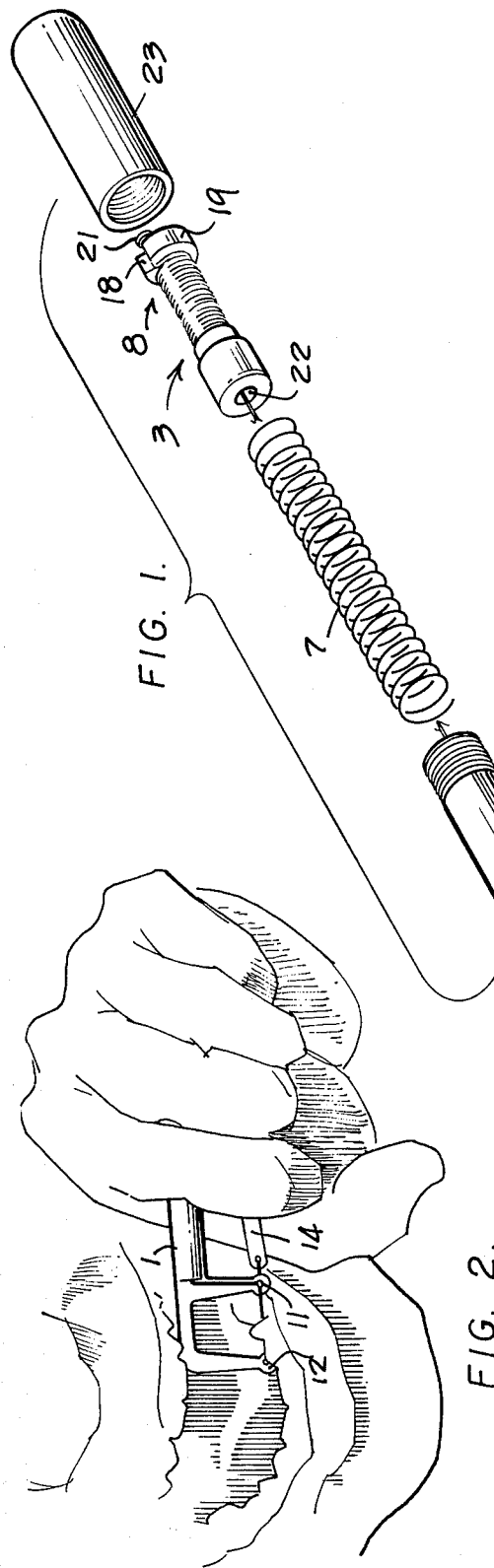
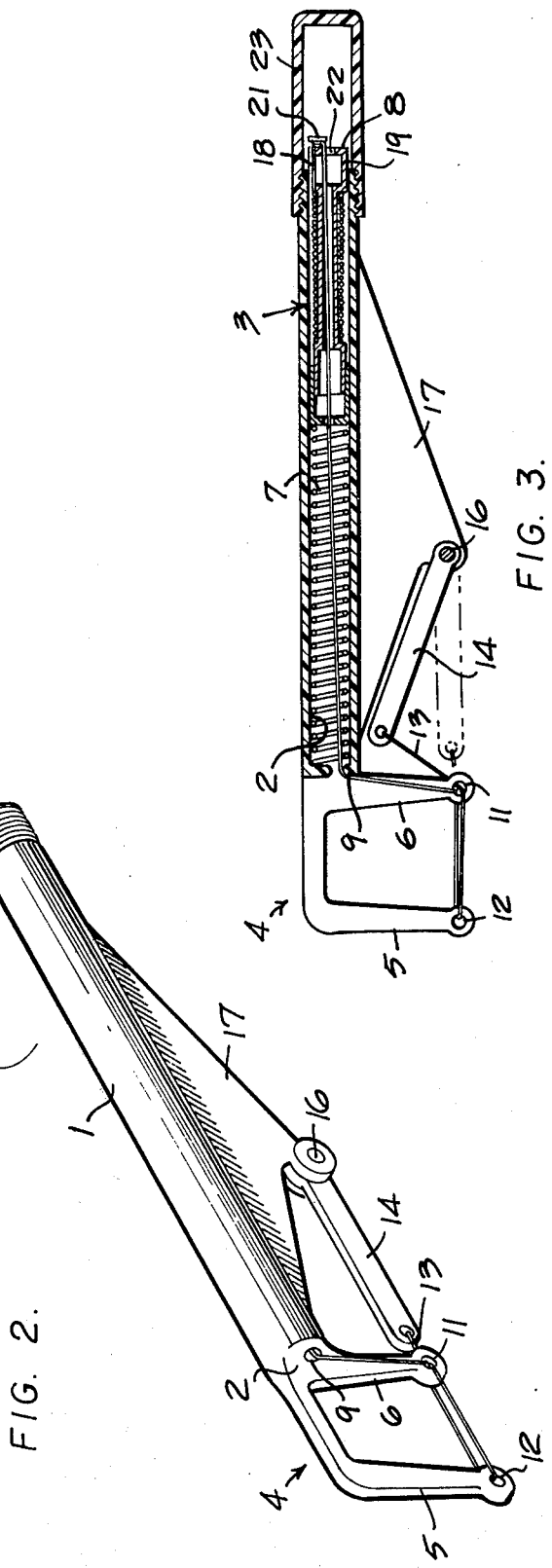

DENTAL FLOSS MANIPULATOR

BACKGROUND OF THE INVENTION

There are many forms of dental floss applicators in the prior art, however, in all those known to applicant it is necessary to reciprocate the applicator in the mouth in order to move the dental floss between the teeth back and forth. The space in the mouth and particularly between the teeth and the tongue is very limited and therefore such reciprocation is inconvenient and not as effective as it should be.

The primary object of the invention is to provide a manipulator whereby the unwound dental floss can be inserted between the teeth and then without reciprocating the handle and the fork fingers the dental floss can be pulled back and forth between the teeth without the necessity to reciprocate or move the handle in the mouth.

BRIEF DESCRIPTION OF THE DRAWINGS

FIG. 1 is a perspective developed view of the dental floss manipulator.

FIG. 2 is a perspective view of the dental floss manipulator in use.

FIG. 3 is a side view with the casing removed showing the manipulator device when the trigger lever is pulled against the action of the spring anchor.

DETAILED DESCRIPTION

The manipulator herein includes a tubular handle 1 the hollow space 2 of which accommodates a spool of dental floss 3 at one end thereof. The other end of the handle is formed into a fork 4 the fingers 5 and 6 of which are so spaced from one another that in use they straddle the teeth of a person. A spring 7 is provided between the spool 3 and the fork 4 so that it bears against the fork 4. Anchor means 8 on the spool 3 anchor the unwound dental floss whereby the spool 3 can be pulled toward the fork 4. The unwound dental floss is threaded around a guide 9 on finger 6 and a guide hole 11 in the lower end of the finger 6 and then through a guide hole 12 in the lower end of the other finger 5. A return free end 13 of the unwound dental floss is attached to the free end of a trigger lever 14 which latter is supported on a pivot 16 on a projection 17 of the handle 1. The handle is formed so that the fork 4 is substantially in the same plane as the axial plane of the handle.

The anchor means 8 include a notch 18 in the periphery of a flange 19 of the spool and grooved button 21 around which the dental floss is wound before it is inserted through an axial hole 22 of the spool 3.

In operation when the trigger 14 is pulled up toward the handle 1 it pulls the unwound dental floss and thereby pulls the spool 3 and compresses the spring 7. When the trigger 14 is released the spring 7 pushes the spool 3 away from the fork 4, thereby reciprocating the dental floss between the teeth of the user. A cap 23 is threaded on the open end of the tubular handle 1 for replacement of the spool 3.

I claim:
1. In a dental floss manipulator,
a handle,
fingers at one end of the handle spaced from one another so as to straddle teeth in the mouth,
anchor means on said handle to anchor unwound dental floss,
resilient means on said handle urging said anchor means toward the other end of said handle,
guiding means for the dental floss on said spaced fingers to extend the dental floss between the fingers thereby to locate said dental floss betwen adjacent teeth,
trigger means movably held on said handle,
said handle being substantially tubular and said fingers being in a plane longitudinal with respect to said handle,
the free end of said dental floss being secured to said trigger means whereby the manipulation of the trigger means in opposite directions against the action of said resilient means reciprocates the dental floss in the space between the teeth in the mouth.
2. The dental floss manipulator specified in claim 1, and said anchor means including a spool of dental floss.
3. The dental floss manipulator specified in claim 1, and said guiding means being holes through said respective fingers.
4. The dental floss manipulator specified in claim 1, and
a spool for said dental floss reciprocable in said tubular handle,
said anchor means releasably anchoring the unwound dental floss on said spool, and said fingers being spaced apart to straddle the teeth in the mouth,
said guiding means on said fingers including holes on the fingers to accommodate the dental floss threaded therethrough, so as to locate the dental floss across the space between the fingers.
5. The dental floss manipulator specified in claim 1, and
said handle having an extension thereon between said other end and said fingers, and said trigger being pivoted on said extension.
6. The dental floss manipulator specified in claim 5, and
a removable closure on said other end of said tubular handle.
7. The dental floss manipulator specified in claim 1, and said free end of the dental floss being threaded first through the guided means nearer to said trigger means and then through the guide means farther from said trigger means and then returned to said trigger means thereby to provide adjacent strands of dental floss reciprocating in opposite directions.

* * * * *